(12) United States Patent
Bodmeier (10) Patent No.: US 7,820,202 B2
(45) Date of Patent: Oct. 26, 2010

(54) EXTENDED RELEASE PARTICLE DISPERSION

(75) Inventor: Roland Bodmeier, Berlin (DE)

(73) Assignee: Laboratorios Farmaceuticos Rovi S.A., Madrid (ES)

( * ) Notice: Subject to any disclaimer, the term of this patent is extended or adjusted under 35 U.S.C. 154(b) by 1907 days.

(21) Appl. No.: 10/378,733

(22) Filed: Mar. 4, 2003

(65) Prior Publication Data

US 2003/0152634 A1     Aug. 14, 2003

Related U.S. Application Data

(63) Continuation-in-part of application No. PCT/DE01/03438, filed on Sep. 4, 2001.

(30) Foreign Application Priority Data

Sep. 5, 2000   (DE)  .............................. 100 44 545

(51) Int. Cl.
  *A61K 9/14*   (2006.01)
  *A61K 9/16*   (2006.01)
  *A61K 9/50*   (2006.01)
(52) U.S. Cl. ..................... 424/489; 424/491; 424/493; 424/502

(58) Field of Classification Search .................. 424/489
See application file for complete search history.

(56) References Cited

U.S. PATENT DOCUMENTS

| 5,278,201 | A | * | 1/1994 | Dunn et al. | .................. 523/113 |
| 5,785,682 | A | * | 7/1998 | Grabenkort | .................. 604/82 |
| 5,945,115 | A | * | 8/1999 | Dunn et al. | .................. 424/422 |
| 2004/0127846 | A1 | * | 7/2004 | Dunn et al. | .................... 604/82 |

OTHER PUBLICATIONS

Merriam-Webster's Collegiate Dictionary. Merriam-Webster Incorporated: Springfield, Massachusetts, 1993, pp. 311.*

* cited by examiner

*Primary Examiner*—Jake M. Vu
(74) *Attorney, Agent, or Firm*—Rick Matos; Innovar, L.L.C.

(57) ABSTRACT

The invention relates to extended release compositions that can be advantageously used as drug products, plant protection agents, in foods or other products. The invention especially relates to liquid compositions in which extended release particles are dispersed. The compositions according to this invention are available in the form of single-dose or multi-dose compositions and as such are produced from liquid preproducts. The invention further relates to kits and methods for producing the compositions and to the preproducts thereof.

48 Claims, 1 Drawing Sheet

EXTENDED RELEASE PARTICLE DISPERSION

CROSS-REFERENCE TO EARLIER FILED APPLICATIONS

The present application is a continuation-in-part of PCT International Patent Application no. PCT/DE01/03438 filed Sep. 4, 2001, which claims the priority of German Patent Application No. 10044545.4 filed Sep. 5, 2000.

FIELD OF THE INVENTION

The invention relates to extended release compositions that can be advantageously used in drug products, plant protection agents, in foods and in other products. The invention especially relates to liquid compositions in which extended release particles are dispersed. The inventive compositions are available in the form of single-dose or multi-dose compositions and as such are prepared from liquid preproducts. The invention further relates to kits and methods for producing the compositions and to the preproducts thereof.

BACKGROUND OF THE INVENTION

The interest in the development of extended release preparations, in particular of those on the basis of biodegradable polymers, has increased significantly in the last years. Drug products based on these compositions can maintain therapeutically effective drug levels for weeks or months with drugs having a low oral bioavailability or a high first pass effect. This is especially applicable for the new generation of highly potent, biotechnologically derived drugs such as peptides and proteins. Daily injections are avoided because of the longer dosing intervals and, therefore, the patient compliance is improved.

In order to retard the release of the active compound, the active compound is embedded in a biodegradable polymer matrix or is surrounded with a polymer shell. The synthetic poly(lactide-co-glycolide) (PLGA) derivatives are predominantly used among water-insoluble polymers for this purpose because of their approval in marketed drug products. The biodegradable polymers are frequently used in drug products in the form of implants or microparticles.

Implants (commercial products: Profact Depot, drug: busereline acetate, Höchst Marion Roussel; Zoladex, drug: gosereline acetate, Zeneca) are mostly cylindrically shaped polymer rods with embedded active compound, which are prepared by melt extrusion or -compression. The disadvantages of these methods are high process temperatures, which can cause degradation of the active compound and problems of homogeneity with low dose active compounds. In addition, the required surgical procedures for implantation or the injection through large needles is not popular with patients.

Biodegradable microparticles (commercial products: Enantone Depot, drug: leuprolide acetate, Takeda Chemicals; Decapeptyl Depot, drug: triptoreline acetate, Ferring) can be injected easier in the form of aqueous dispersions of the microparticles and are therefore preferred by the patients when compared to implants. These microparticles are prepared by various methods, such as the solvent evaporation- or solvent extraction methods (e.g. EP 0 190 833), organic phase separation- (EP 0 052 510) or spray drying methods (EP 0 505 966).

In the solvent evaporation method, which is frequently used for the preparation of biodegradable microparticles, a drug is dissolved or dispersed in a solution of a biodegradable polymer (e.g., PLGA in methylene chloride). This drug-containing polymer phase is then emulsified in an external aqueous phase and forms drug-containing polymer droplets. The microparticles are obtained after evaporation of the solvent or after diffusion of the solvent in the external phase through the solidification of the polymer and are then separated from the aqueous phase (e.g., by filtration) and dried.

In the organic phase separation method, the coacervation into particles is induced by the addition of a nonsolvent (e.g., silicone oil) to a dispersion of the active compound in an organic polymer solution. The microparticles are hardened, filtered, washed and dried.

In the spray drying method, the microparticles are obtained by the spraying/drying of the active compound-containing organic polymer solution into a heated air stream and by the separation in a cyclone.

Commercially available biodegradable microparticle products therefore consist of a dry powder of the microparticles and an aqueous suspension vehicle, which is stored separately. The microparticles in dry form and the aqueous suspension vehicle are stored separately, for example in two-chamber syringes or in two ampoules, because of the hydrolytic instability of the biodegradable polymers. The biodegradable polymer would, during storage, hydrolytically degrade in direct contact with the aqueous suspension vehicle. The solid microparticles are then suspended in the aqueous suspension vehicle just prior to the administration and are then injected primarily subcutaneously or intramuscularly.

The described microencapsulation methods and the resulting microparticles can have various problems: (1) the use of toxic organic solvents and the solvent residuals in the product; (2) a large number of process- and formulation variables, which influence the properties of the microparticles and which have to be validated; (3) a low encapsulation efficiency and product yield; (4) the necessity of costly measures for the aseptic preparation or the risk of changes in the particle properties after irradiation of the final product; (5) stability problems during storage of the particles, for example changes in the release profile because of aging processes. In most instances, the microparticles are stored separately from the aqueous suspension vehicle in ampoules or two chamber syringes. This storage form requires a reconstitution step just prior to administration. The suspension of the microparticles and the subsequent injection can also cause difficulties due to agglomeration of the particles, residual microparticles in the syringe, clogging of the needle, etc.

WO 98/55100 describes compositions, which avoid some of the problems seen during the preparation and administration of microparticles and implants. These compositions form particles and/or implants after placement in the body of a human or an animal. The compositions comprise an inner, polymer-containing carrier phase and an external phase, which is immiscible or partially immiscible with the carrier phase, wherein the viscosity of the carrier phase is changed after a change in ambient conditions (e.g., placement in subject) such that a solidification of the polymer into particles or implants occurs.

According to WO 98/55100, an active compound-containing dispersion, consisting of an inner drug-containing carrier phase and a second external phase (e.g., an oil) may be prepared and be placed into the body. The inner carrier phase comprises a solution of a polymer (e.g., PLGA) and a solvent. The inner phase solidifies after placement in the body, for example through solvent diffusion in the body fluids or diffusion of body fluids into the carrier phase. For example, in the case of biodegradable polymers, the dispersion may be injected i.m. or s.c. The inner phase solidifies in contact with body fluids and forms particles.

A need exists for extended release preparations, which do not have the disadvantages inherent in the known art, for example the very tedious large-scale production of microparticles. In particular, there is a need for compositions of extended release particles, which are prepared just prior to administration from preproducts.

SUMMARY OF THE INVENTION

The object of the present invention is to provide a liquid composition of extended release particles, wherein the composition does not have the disadvantages inherent in the known art and which can be administered as single- or multi-doses in a simple manner.

The present invention provides a ready-to-use single- or multi-dose of a composition with extended release of an active compound in the form of a dispersion of extended release particles, wherein the extended release particles are formed by mixing at least two liquid preproducts, which are present in portions suitable for the preparation of the single- or multi-dose composition.

According to one aspect of the invention, the ready-to-use dispersion composition comprises solidified particles that provide an extended release of one or more active compounds; wherein the extended release particles are formed by mixing at least two liquid preproducts, which are present in portions suitable for the preparation of the single- or multi-dose composition;

the first liquid preproduct comprises a carrier material that solidifies to form the extended release particles and, optionally, a biocompatible solvent or solvent mixture; and the second liquid preproduct comprises a biocompatible liquid within which the first liquid preproduct forms the extended release particles.

Another aspect of the invention provides a method for the preparation of a ready-to-use single- or multi-dose dispersion of extended release particles, the method comprising the steps of:

providing at least two liquid preproducts;

providing at least one active compound in dissolved, emulsified and/or suspended form in at least one of the at least two liquid preproducts;

mixing at least two liquid preproducts, which are present in portions suitable for the preparation of the single- or multi-dose dispersion, to form a dispersion of a first liquid preproduct within a second liquid preproduct; wherein the first liquid preproduct comprises a carrier material that solidifies to form the extended release particles and, optionally, a biocompatible solvent or solvent mixture; and the second liquid preproduct comprises a biocompatible liquid within which the first liquid preproduct forms the extended release particles.

Still another aspect of the invention provides a kit for the preparation of a ready-to-use single- or multi-dose pharmaceutical dispersion of extended release particles, the kit comprising at least two liquid preproducts each of which is present in a portion for the preparation of a single- or multi-dose composition; wherein:

at least two of the preproducts are liquid and wherein the extended release particles are formed by mixing the preproducts;

a first liquid preproduct comprises a carrier material that solidifies to form the extended release particles; and a second liquid preproduct comprises a biocompatible liquid within which the first liquid preproduct forms the extended release particles.

A ready-to-use composition according to the invention is defined as an immediately usable or administrable composition of particles dispersed within a biocompatible liquid, optionally wherein the particles have been formed in the same or substantially the same liquid in which they will be administered. The composition comprises at least one active compound in the particles and one or more other materials. A ready-to-use composition is ready for administration in about at least two minutes, at least five minutes, at least 10 min, at least 20 min, at least 30 min, at least 45 min, at least 60 min, at least 90 min, or at least 120 min. The ready to use composition is generally suitable for administration for a period of up to two hours, four hours, 6 hours, 10 hours, 18 hours, 24 hours or 48 hours and in some cases up to a few days longer.

According to the invention, the composition is provided as a dose or portion, either as a single dose or a defined multi-dose. A multi-dose consists of a multiple (e.g., 2 times, 10 times, or 50 times) of the single dose.

Figure 1:
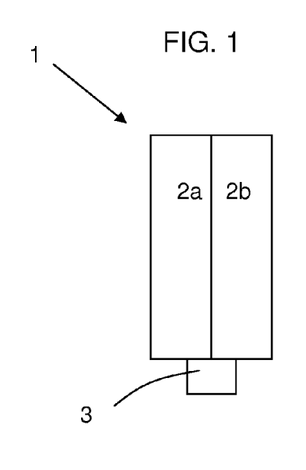
FIG. 1 depicts separate chambers (2a, 2b) of a primary packaging (1), wherein the chambers are connectable (3) with each other to permit mixing of the preproducts.

Specific embodiments of the invention include those wherein: 1) the extended release particles are formed by mixing the preproducts just prior to administration to a subject; 2) the extended release particles are further processed by concentrating the dispersion, changing the composition of the liquid in which the particles are dispersed; 3) the dispersion is administered to the subject without further processing; 4) wherein one or more additional solid or liquid preproducts are used for the preparation of the composition and/or formation of the extended release particles; 5) the liquid preproducts are provided in separate chambers as primary packaging within a device; 6) the liquid preproducts are provided in separate containers in a kit; 7) the first liquid preproduct is provided as a dispersion of a carrier material within a liquid; 8) the first liquid preproduct is provided as a dispersion of a liquid within a solution comprising carrier material; 9) the first liquid preproduct further comprises drug containing particles or droplets; 10) the preproducts are provided in separate chambers (2a, 2b; FIG. 1) of a primary packaging (1), wherein the chambers are connectable (3) with each other to permit mixing of the preproducts; 11) the preproducts are provided in sterile form and mixing of the preproducts is conducted aseptically; 12) the carrier material is a polymer that is soluble, partially soluble, or insoluble in aqueous fluids, a biocompatible and/or biodegradable polymer, a protein, a lipid or a wax, another non-polymeric material or a combination thereof; 13) the carrier material comprises polylactide or a polylactide-derivative; 14) the first liquid preproduct comprises a solvent or solvent mixture that dissolves the carrier material; 15) the second liquid preproduct comprises water as a major component; 16) an active compound in the dispersion is provided in dissolved, emulsified and/or suspended form in at least one of the first and second liquid preproducts; 16) the composition further comprises one or more substances selected from the group consisting of viscosity-increasing substances, substances that cause a thixotropic effect, stabilizers, emulsifying agents, release modifying agents, substances that change the residence time at the site of administration, bioadhesive materials, penetration enhancers, substances that reduce the solubility of the active compound, or substances that influence formation of the particles; and/or 17) one or more active compounds are independently included in the first liquid preproduct and/or the second liquid preproduct.

Other features, advantages and embodiments of the invention will become apparent to those skilled in the art by the following description, accompanying examples and appended claims.

DETAILED DESCRIPTION OF THE INVENTION

The composition according to the present invention results in the extended release of an active compound. "Extended release" according to the present invention means all kinds of release profiles except a rapid, unrestricted release, for example a controlled release, a multiphase release, a retarded release and so on. An extended release is provided, if only one or if all active compounds present in the composition are released in an extended release fashion. The release can take place for several hours, a day, several days, a week, more than one week, a month, more than one month, a year, or more than one year.

A dispersion of extended release particles according to the present invention is a multiphase system with a liquid (including low, medium and high viscosity liquids) external phase and an inner phase of solid or semisolid extended release particles distributed therein. The particles comprise one or more active compounds and release it in an extended release fashion. The term particle is broad, for example with respect to shape, size, consistency and structure. The particle size depends among other factors on the shear forces during mixing, the mixing device, the viscosities of the first liquid carrier material-containing preproduct (dependent for example on the concentration and molecular mass of the carrier material) and the second liquid preproduct (e.g., addition of viscosity-increasing substances to an aqueous phase) and the solidification process of the particles. The particle size covers a range from larger than 1 mm down to the colloidal range (<1 nm, nanoparticles, nanocapsules). For parenteral depot formulations, particle sizes less than 100 μm are usually preferred. The particles form through the solidification of the liquid carrier material-containing preproduct during the mixing process. The particles may also have domains with different degrees of solidification (consistency), the particle surface could for example have a different degree of solidification than the inner part of the particles. The structure of the particles may be manifold, for example, it may have reservoir- (capsules) or matrix-structures or may also have different pore-/channel structures within the particles, or may consist of agglomerates of the particles. A variety of different particle structures is possible.

The composition according to this invention is made from at least two liquid preproducts. The term "liquid" encompasses a broad viscosity range of the preproducts, for example, besides thin liquids also semisolid, gel-like and paste-like preproducts. The first liquid preproduct comprising carrier material can be present as a homogeneous or heterogeneous liquid, e.g., solution, dispersion, emulsion, or suspension. Prior to mixing of the first liquid preproduct and the second liquid preproduct, the carrier material in the first liquid preproduct is present in a non-solid form. Mixing of the liquid preproducts causes formation of hardened particles.

The extended release particles are formed by mixing at least two liquid preproducts that are present in portions suitable for the preparation of the single- or multi-dose composition. Accordingly, more than two preproducts may be used for the preparation of the extended release particles, however, at least two of them are liquid. One or more additional preproducts may be liquid or solid. According to the present invention, the preproducts are already present in portions suitable for the preparation of the single- or multi-dose composition, for example as a kit. Preferably, the preproducts are present in portions suitable to form a single dose.

In contrast to the elaborate preparation techniques for extended release particles known in the art, the particles according to the present invention may be prepared from the preproducts just prior to administration, for example by skilled medical personnel and are then injected (e.g., by i.m. or s.c. injection). The invention requires the preparation of the extended release particles and administration thereof in the same medium without separation of the particles from the medium prior to administration. The present invention does not require the drying and resuspension of microparticles prepared with microencapsulation processes known in the art (e.g. solvent evaporation method, organic phase separation, spray drying).

A composition according to the present invention may for example be prepared from a drug-containing solution of poly (lactide-co-glycolide) in a biocompatible solvent such as ethylacetate as the first liquid preproduct in one syringe and a separately stored aqueous dispersion vehicle (e.g., water for injection, Tween 80, sodium carboxymethylcellulose) as the second liquid preproduct in a second syringe. The particle dispersion is formed prior to administration by mixing the two liquid preproducts through a connector, which connects the two syringes (or which are otherwise connected or screwed together), by pushing forward and backward the plungers of the syringes. A dispersion of the polymer-containing first liquid preproduct in the aqueous second liquid preproduct is thus formed. The drug-containing polymer particles are thereby formed after the formation of the dispersion, for example, by the solidification of the dispersed polymer-containing first liquid preproduct, whereby the solidification is caused by the solvent diffusion from the dispersed first liquid preproduct into the aqueous second liquid preproduct and the diffusion of the aqueous phase in the dispersed polymer-containing first liquid preproduct. This particle dispersion, which, in the case of using a solvent, also comprises this solvent, can then be administered to a subject, e.g., injected s.c. or i.m. into the patient. The administered particles release the drug therein in an extended release fashion.

It is preferred that the preparation of the composition and the formation of the extended release particles are performed just prior to administration, that is within a time interval prior to administration, within which regular, preformed extended release particles are normally reconstituted in a dispersion vehicle. Particularly preferred is the preparation on the day of administration, especially within 2 to 120 min prior to administration.

The formation of the particles may be caused by a concentration of the polymeric carrier material, a precipitation of the carrier material, a diffusion of the polymer solvent into the second liquid preproduct, a temperature change, a pH-change, a change in ionic strength or ion type, or through a combination of two or more of the mentioned processes.

It is preferred that the composition with the extended release particles, which is obtained by mixing the preproducts, is administered without further processing steps, especially without concentrating the particles or their partial or complete separation from the liquid phase by drying, centrifugation, dialysis, filtration, etc.

Figure 2:
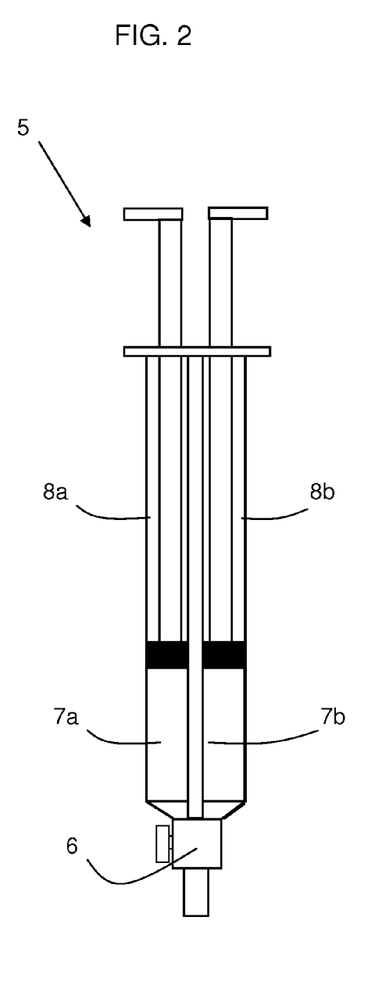
FIG. 2 depicts a multichamber syringe (5) with separate chambers (8a, 8b) and mixing means (6).

It is preferred that the liquid preproducts are provided in separate chambers (FIG. 1 (2a), (2b)) as primary packaging (1) during shelf-life. The separate chambers (8a, 8b) may be part of the same or of different devices, for example of different syringes or of a multichamber syringe (FIG. 2; (5)). The liquid preproducts may be mixed prior to administration by connecting/-screwing together the syringes or within the multichamber syringe. For example, two syringes could be connected with a connector (e.g., made of plastic, glass or metal). The two syringes are plugged in the two open sides of a connector with a defined bore size. The two syringes could also be screwed together directly, for example, if one syringe has a female and the other one a male Luer Lock. The extended release particle dispersion is then formed by mixing the preproducts by pushing the formulations forward and backward several times within the two syringes by pushing the two syringe plungers forward and backward. The plungers are generally moved forward and backward (one mixing cycle) sufficiently often in order for the extended release dispersion to form. In general, 10 mixing cycles are sufficient, however, depending on the formulation, more or less mixing cycles may be necessary. Alternatively, the preproducts (7a, 7b) could be mixed (6, mixing means) within a multichamber syringe, which exists in various designs. The preproducts may of course also be stored in commonly used containers (e.g. ampoules or glass vials) and may then be mixed just prior to administration. In the case of injectable compositions, the preproducts should be provided in a sterile package and the chambers should be suitable to enable the mixing process under aseptic conditions.

In general, one of at least two liquid preproducts comprises a polymeric carrier material, which is dissolved and/or dispersed in this preproduct or forms the preproduct itself. The solidification of the carrier material is caused by mixing of at least the first and second preproducts, whereby the extended release particles are formed. The carrier material therefore forms an important component of the particles.

A particle dispersion can also be made as described in the examples below. For example, a first liquid preproduct can comprise a dispersion of unsolidified carrier material in a liquid. The droplets of the dispersion are then solidified by mixing of the first and second liquid preproducts. Alternatively, a first liquid preproduct can comprise a dispersion of liquid droplets within an unsolidified carrier material solution, e.g., a water in oil emulsion in which the carrier material is present in the oil phase. The first liquid preproduct is then dispersed within the second liquid preproducts.

The first liquid preproduct should be immiscible, substantially immiscible, or at least partially immiscible with the second liquid preproduct. The first and second liquid preproducts should be sufficiently immiscible to permit formation and hardening of the dispersion of particles. Alternatively, the carrier material in the first liquid preproduct should be immiscible/insoluble, substantially immiscible/insoluble or at least partially immiscible/insoluble with the second liquid preproduct.

The carrier material is especially important for the retardation of the release of the active compound. Suitable carrier materials are, depending on the specific requirement (for example the release time), water-soluble or water-insoluble polymers, polymers soluble in aqueous fluids, biocompatible and/or biodegradable polymers, proteins, lipids, waxes, nonpolymeric materials or a combination of several of these substances.

The carrier materials are of synthetic, semisynthetic and natural origin. Preferred carrier materials include cellulose derivatives (e.g., cellulose acetate, ethyl cellulose, cellulose acetate phthalate, cellulose ethers such as hydroxypropylmethyl cellulose), acrylate-derivatives (e.g., Eudragits, poly(methylmethacrylate), cyanoacrylate), biocompatible and biodegradable polymers such as polyanhydrides, polyesters (e.g. polylactide, polyglycolide, polycaprolactone, polyhydroxybutyrate- or valerate or derivatives of these polymers, such as poly(lactide-co-glycolide)/polyethyleneglycol blockpolymers), polyamines, polyaminoacids, polyorthoesters, polyurethanes, poly(ortho)carbonates, polyphosphazenes, polyacetals, polyketals, polyalkyleneoxalate, polyalkylensuccinate, polyoxyethylene-oxypropylene, polysaccharides (e.g., sodium alginate, chitosan, or chitin), polyethyleneglycol, polyvinylpyrrolidone, lipids (e.g., waxes, fats, glycerides) and copolymers or terpolymers or a combination of two or more of these carrier materials. Many carrier materials are described in the literature and are known to the skilled person in the art as useful components for extended release particles. Polylactide, polylactide-derivatives, polyanhydrides and polyorthoesters are particularly useful carrier materials.

In general, namely, if the carrier material itself is not a liquid or liquefiable, the carrier material-containing preproduct comprises water and/or an organic solvent, such as ethanol, acetone, methylethylketone, butanol, ethylformate, acetic acid, lactic acid, pentanol, n- or iso-propanol, tetrahydrofuran, triethylcitrate, citratesters, phthalate esters, isopropylmyristate, triacetin, tributyrin, propylene glycol, glycerol, polyethylene glycol, 2-ethoxyethylacetate, ethylacetate, methylacetate, ethyllactate, ethylbutyrate, benzylalcohol, benzylbenzoate, dimethylformamide, dimethylsulfoxide, dimethylacetamide, propylenecarbonate, glycofurol, solketal, oleic acid, 2-pyrrolidone, N-methyl-2-pyrrolidone, caprolactame, or an oil, or a plasticizer or a combination of two or more of these solvents as a vehicle for the carrier material. The solvent or solvent mixtures are generally used to dissolve the carrier material, for example to form a polymer solution.

In particular, solvents from the "Draft guideline of the international conference on harmonization on impurities—residual solvents" may be suitable. The limits on maximum allowable solvent quantities in humans are listed in the guidelines and are one of several tools for the selection of solvents. The solvent has to be biocompatible and should preferably dissolve the carrier material. Combinations of solvents and nonsolvents for the carrier material may also be used. Solvent mixtures may also be selected based on their solvent quality for the carrier material or their miscibility with aqueous phases. The solvent selection may for example influence the solidification of the carrier material and the miscibility with body fluids or with a second liquid preproduct. Compared to microencapsulation methods known in the art, this invention does not use toxic organic solvents, but only biocompatible solvents. For example, the most commonly used, but toxic solvent for the preparation of microparticles with the solvent evaporation method, methylene chloride, is not used as a solvent in this invention.

In the case of polymer solutions (first liquid preproduct), the solvent/solvent mixture should preferably be partially and not completely miscible with the second liquid preproduct (e.g., solubility of ethylacetate in water is approx. 10% and of triacetin in water approx. 8%). Particles must be formed during the mixing process and this determines in each case the upper and lower limit in the miscibility of the solvent/solvent mixture present in the first, carrier-containing preproduct with the second liquid preproduct. Because of this partial miscibility, the solvent diffusion from the dispersed carrier material (e.g., polymer)-containing first liquid preproduct in the second liquid preproduct results in the solidification of the dispersed first liquid preproduct or carrier material into the extended release particles. Besides the miscibility of the solvent/solvent mixture with the second liquid preproduct, the degree of solidification depends among other factors also on the quantitative ratio of the two liquid preproducts. The solidification of the dispersed first liquid preproduct into extended release particles during the formation of the dispersion occurs preferably at a lower phase ratio of the first liquid carrier material-containing preproduct to the second liquid preproduct, while the dispersed carrier material-containing preproduct would remain liquid at a higher phase ratio. A lower ratio of the first liquid carrier material-containing preproduct to the second liquid preproduct means for example a ratio of 1 part of the first liquid carrier material-containing preproduct to 10 parts of the second liquid preproduct (phase ratio of 1:10), while, for example, a higher ratio would be 1 part of the first liquid carrier material-containing preproduct to 1 part of the second liquid preproduct (phase ratio of 1:1). In general, a higher ratio of the two liquid preproducts is sufficient, when the miscibility of the solvent/solvent mixture present in the first carrier material containing liquid preproduct and the second liquid preproduct is higher. In contrast, a lower miscibility requires a lower ratio, meaning proportionally more second liquid preproduct for the formation of the extended release particles, otherwise liquid droplets and not particles would form from the dispersed first liquid preproduct. The formation of the extended release particles can easily be proven by mild centrifugation of the dispersion. The extended release particles can be resuspended and therefore do not agglomerate/coalesce. If the dispersed first liquid preproduct coalesced, this would indicate no formation of solid extended release particles.

The viscosity of the carrier material-containing preproduct may be influenced by the carrier material itself (e.g., its molecular mass, concentration etc.) and also by the type of solvent, if the carrier material is dissolved in a solvent within the first liquid preproduct. In the case of poly(lactide-co-glycolide) solutions, the workable polymer concentration in the first liquid preproduct may be influenced among other factors by the molecular mass of the polymer. Lower molecular mass polymers result in higher concentrated polymer solutions (first liquid preproduct). Under certain conditions, higher concentrated solutions of low molecular mass polymers may result in a better entrapment of the active compound and in a better retardation of the release of the active compound. Highly concentrated solutions (>50%) may be used with poly(lactide-co-glycolide)-polymers of low molecular mass.

The second liquid preproduct may comprise as major components natural, semisynthetic or synthetic lipids, oils or waxes, such as cottonseed oil, soybean oil, safflower oil, hydrated peanut oil, olive oil, castor oil, tryglyceride mixtures (such as Miglyol), monoglyceride (such as glycerolmonooleate), silicone oil, isopropylmyristate, ethyloleate, paraffins, water, glycerol, propylene glycol, polyethylene glycol or a combination of two or more of these substances. A particularly preferred component is water. In general, components of the first liquid preproduct (for example the solvent) are partially miscible with the second liquid preproduct. Upon mixing of the preproducts, the second liquid preproduct forms the major component of the dispersion vehicle (external phase) of the extended release particle dispersion.

According to the invention, the active compound is for example a drug, a peptide- or protein drug, an oligonucleotide or gene therapeutical agent and it can be a drug belonging to the group of antibiotics, anti-inflammatory agents, antiinfectives, antiparasitics, hormones, immunologically active compounds, vaccines, immunomodulators, immunosuppressant, anticancer agents, diuretics, drugs for the gastrointestinal tract, for the heart/circulation, for the respiratory tract, growth factors, interferons, analgetics, local anaesthetics and/or neuropharmaceuticals. Possible drugs are for example listed in WO 00/24374 or WO 98/27963. In addition, if necessary, two or more active compounds, of which at least one is released in a retarded fashion, may be administered with a composition according to this invention. Besides drugs for human and veterinary applications, also substances, which are used for agricultural purposes, in households, in the food, cosmetic and chemical industry and other industrial branches may be used as active compounds.

According to the invention, the active compound is preferably dissolved, dispersed, suspended or emulsified in the first liquid carrier material-containing preproduct; however, it may also be present additionally or exclusively in the second liquid preproduct. However, after the mixing of the liquid preproducts, the active compound has to be entrapped in the extended release particles in order to get a retardation in the release of the active compound. Unentrapped active compound present in the dispersion vehicle (consists primarily of the second liquid preproduct) of the dispersion is available in nonretarded form, which may for example be interesting to achieve the desired drug levels in the body rapidly. The physical state of the drug in the first liquid carrier material-containing preproduct may be determined by the selection of the solvent/solvent mixture. With more active compounds, it could be advantageous, that one of the active compounds is (at least predominantly) in the first preproduct and another active compound is (at least predominantly) in the second preproduct. In the case of stability problems, an active compound may also be stored separately as part of an additional liquid or solid preproduct, which may be added to one of the two previously mentioned liquid preproducts or to both for the preparation of the extended release particles. One possibility is for example the separate storage of the solid active compound, and the first and second liquid preproducts within several different syringes. According to the invention, the active compound may also be added in aqueous solution to one of the liquid preproducts prior to mixing it with the other liquid preproduct. This addition of the active compound-containing aqueous phase may also be performed just immediately prior to the formation of the extended release particles. In this case, the aqueous active-compound containing phase is mixed with the first liquid carrier material containing preproduct. A w/o-emulsion forms, or the active compound may finely precipitate upon addition of the aqueous solution to the first liquid preproduct. This mixture is the mixed with the second liquid preproduct to form the extended release particles. This method enables for example the encapsulation of water-soluble active compounds. Other solvents may be used instead of water.

In addition, the preproducts may comprise other substances such as viscosity-increasing substances, substances, which cause a thixotropic effect, stabilizers, emulsifying agents, release modifying agents, substances, which change the residence time at the site of administration, bioadhesive materials, penetration enhancers, substances, which influence the solubility of the active compound, or substances, which influence the particle formation (e.g. particle structure) in order to influence the properties of the composition with known techniques in pharmaceutical technology, for example with the aim to release the active compound in a prolonged fashion at the site of administration and/or to avoid an initial rapid release of the active compound at the site of administration. In particular, stabilizers, such as emulsifying agents, which are added to the first and/or the second liquid preproduct, may be necessary. The emulsifying agents include among others polyethyleneglycol- fatty acid esters, -fatty acid ethers, -sorbitan fatty acid esters, sorbitan fatty acid esters, partial fatty acid esters of multivalent alcohols or sugars, lecithins, phospholipids, poloxamers, proteins and cellulose-derivatives, for example cellulose ethers.

In addition, the active compound may be present in encapsulated form in the liquid carrier material containing preproduct, for example in the form of microparticles, microcapsules, colloidal particles (e.g., nanoparticles, nanocapsules, liposomes), it may also be bound to ion exchange resins, cyclodextrins or to other complexing agents. In the case of water-soluble active compounds (for example peptide-/protein-/oligonucleotide drugs), a reduction in the solubility of the active compound in aqueous fluids is possible through the complexation with oppositely charged low- or higher molecular weight molecules (for example cationic/anionic/amphoteric lipids, polysaccharides or proteins). This may result in a better entrapment of the active compound within the extended release particles (for example in the case of an external aqueous phase being used as the second preproduct) or also in an additional retardation in the release. These poorly water-soluble drug complexes or-salts may be provided as starting substances or they could also be formed during the formation of the extended release particles. The poorly soluble complex may thereby be entrapped in, or bound to, or adsorbed to the extended release particles.

The entrapment of the active compound in the extended release particles depends on many factors, for example on its solubility/wettability in the first or in the second liquid preproduct. In order to achieve a sufficient loading of the particles, the person skilled in the art may use a variety of galenical tools, which are known from the literature on disperse systems, for example on microparticles. The solubility of the active compound in the second liquid preproduct, which generally forms the dispersion vehicle for the particles (external phase of the dispersion) can for example be reduced by the addition of osmotically active substances or by substances, which influence the pH.

A composition according to this invention provides an extended release of the active compound at the site of administration. The release of the active compound may be influenced among other factors by the particle properties (such as size, structure, degree of solidification), the loading with active compound, the solubility of the active compound, the physical state of the active compound (e.g. polymorphic form, complex formation), the carrier material und the concentration of the carrier material. In addition, release modifying agents such as hydrophilic or lipophilic substances of inorganic, organic, or polymeric nature may be incorporated. Also the structure of the particles (e.g. porosity) may influence the release and may be influenced by the selection of the first carrier material containing preproduct and the second liquid preproduct and appropriate additives (see literature on the preparation of microparticles by the solvent evaporation method). The frequently unwanted burst-effect (initial rapid release of the active compound) may be modulated with substances and processing steps known to the person in the art.

Compositions according to this invention are preferably provided (for example through the selection of substances and the pretreatment of the preproducts, e.g. aseptic preparation) for parenteral (e.g., i.v., i.m., s.c., i.a.), peroral, rectal, buccal, ophthalmic, pulmonal, vaginal, nasal, local, sublingual, periodontal, or transdermal administration or for the placement in body cavities and /or on body surfaces. Compositions according to this invention may also be provided for the treatment of soft- and hard tissue defects, for example as scaffolding, for tissue regeneration, as a tissue glue, or for the filling of body cavities, or for the treatment of wounds. In the case of internal or external wound treatment, a composition according to the invention may be placed onto various, medically used, textile fabrics prior to administration.

Preferably, the extended release particle dispersions are administered unchanged and without further processing steps immediately after preparation. Therefore, ready-to-use extended release particle dispersions are prepared and not larger batches of particle dispersions, which then still have to be filled in single unit containers prior to injection.

The composition may be administered in body cavities or on body surfaces by methods known to the person skilled in the art (e.g., by injection or by spraying-on or -in). After administration of the extended release particle dispersion, a further change in consistency of the particles may occur by the mechanisms described above (for example a further solidification, which may also occur in different domains within the particles). Also, a softening of the particles or a coalescence of the particles may be possible under certain circumstances.

Another aspect of the invention is a method for preparation of the compositions described above.

In this method, at least two liquid preproducts, which are present in portions suitable for the preparation of a single- or multi-dose composition, are provided in one or more steps in a way such that the mixing of the preproducts by the user results in the formation of the extended release particles.

After the preparation of the extended release particle dispersion, it is preferably administered without changing the composition of the active compound/other substances. However, it also possible, to concentrate the particles within the second, normally external phase of the dispersion, by separating a part of the second phase or by partially or almost fully replacing the second phase with another external phase, which is for example free of solvent and of active compound. Many possibilities exist for the preparation of the particles. After formation of the particles, the second liquid preproduct can be partially or substantially completely separated from the particles and replaced. Also, the dispersion of particles can be concentrated by removal of part of the liquid in which the particles are dispersed. For example, removal can be done by filtration and/or decanting.

A method for the injection of an extended release particle dispersion according to this invention comprises a) the mixing a carrier material-containing first liquid preproduct with a second liquid preproduct, b) the solidification of the carrier material-containing first liquid preproduct and the formation of extended release particles during this mixing and c) the injection of the extended particle dispersion shortly after the mixing process.

A further advance of the invention are kits, which are arrangements of preproducts, which are matched to each other and which are, if applicable, stored together in a secondary package for the preparation of compositions according to this invention. Therefore, a kit according to this invention comprises at least two liquid preproducts, which are present in portions suitable for the preparation of a single- or multi-dose composition, wherein at least two of the preproducts are liquid and wherein the extended release particles are formed by mixing the preproducts.

In principle, the kit of the invention, which may be distributed by a manufacturer (for example a drug manufacturer) does not already comprise extended release particles (e.g. microparticles). The particles are prepared just prior to administration (e.g., injection) by the user (e.g., medically trained personal) in the form of an administrable (e.g., injectable) particle dispersion by mixing two liquid preproducts. This extended release particle dispersion is then administered shortly after preparation (preferably within several minutes, or within a few hours). When compared to currently available microparticle products, this invention eliminates the complicated large scale manufacturing of microparticles, which has the above-described problems.

The kit can further comprise other limits to permit additional minimal processing of the dispersion. The can include concentrating means that permit concentration of the dispersion, such as by removal of some of the excess liquid in the dispersion. Concentrating means can include a filter or centrifuge. The kit can also include liquid exchanging means by way of which the liquid of the dispersion can be replaced with another liquid. For example, if the liquid in which the dispersion is initially formed is to be replaced, the dispersion might be filtered, centrifuged or decanted. Then, the second liquid would be added to the filtered, centrifuged or decanted mass of particles to form a second dispersion.

When an active compound is included in the kit, the active compound can be present within or separate from the liquid preproducts in the kit. The active compound can be provided in dissolved, emulsified and/or suspended form in at least one of the first and second liquid preproducts. Alternatively, the active compound can be present in any form in a container or chamber separate from the liquid preproducts.

Since additional preproducts can be incorporated into the dispersion, the kit can comprise one or more other/additional preproducts. These additional preproducts are independently upon each occurrence included within the first and/or second liquid preproduct, or separate from the first and/or second liquid preproducts. Exemplary preproducts include viscosity-increasing substances, substances that cause a thixotropic effect, stabilizers, emulsifying agents, release modifying agents, substances that change the residence time at the site of administration, bioadhesive materials, penetration enhancers, substances that reduce the solubility of the active compound, or substances that influence formation of the particles. Also an active compound and/or a carrier material in solid form can form other/additional preproducts.

The composition of the invention can be adapted for administration by routes such as parenteral, peroral, rectal, buccal, ophthalmic, pulmonary, vaginal, nasal, local, sublingual, periodontal, topical, intralesional or transdermal administration. The composition can be administered for the treatment of soft- and hard tissue defects, for the treatment of wounds, for use in tissue regeneration, for use as a tissue glue or for the filling of body cavities. The proper route of administration will be selected as needed according to basic pharmaceutical and pharmacological principles and according to the desired method of administration of a drug or drugs being administered. In one specific embodiment, the dispersion composition is administered by injection after formation of the dispersion.

The following examples should not be considered exhaustive, but merely illustrative of only a few of the many embodiments contemplated by the present invention. The methods described herein can be followed to prepare extended release particle dispersions according to the invention.

EXAMPLE 1

Preparation of Particles from Polymer Solution and Biocompatible Liquid

A solution of poly(d,l-lactide-co-glycolide) (75/25, RG752 or 50/50, RG 502H or 503H from Böhringer Ingelheim) (40% w/w) in ethyl acetate (syringe 1) (200μl) (first liquid preproduct) is mixed with an aqueous phase (water for injection, Tween 80- or alternatively Pluronic F 68-, Na carboxy methylcellulose) (syringe 2) (2ml) (second liquid preproduct) by connecting the two syringes with a connector or by screwing the two syringes together and by pushing the plungers forward and backward (25 mixing cycles). The extended release particles are thereby formed, which are dispersed in the aqueous phase and which are ready to be injected.

EXAMPLE 2

Preparation of Particles from Polymer-containing Dispersion or Solution and Biocompatible Liquid Like example 1. In addition, a drug (estradiol, bupivacaine HCl, or leuprolide acetate) is dissolved or dispersed in the poly(d,l-lactide-co-glycolide) solution (first liquid preproduct) prior to mixing with the aqueous phase (second liquid preproduct) and formation of the extended release particles.

EXAMPLE 3

Preparation of Particles from Polymer-containing Dispersion and Biocompatible Liquid Like example 1. In addition, an aqueous leuprolide acetate solution is dispersed in the poly(d,l-lactide-co-glycolide) solution to form a w/o (water/oil) emulsion, which is the carrier material containing first liquid preproduct such that the aqueous droplets of the emulsion contain a majority or all of the leuprolide acetate solution. The amount of leuprolide acetate solution should be sufficiently low to permit formation of a water in oil emulsion rather than an oil in water emulsion. Then another aqueous phase (the second liquid preproduct) is mixed with the first liquid preproduct to form the extended release particles as a dispersion in the aqueous phase.

EXAMPLE 4

Preparation of Particles from Polymer-containing Liquid and Biocompatible Liquid Like example 1. In addition, a water-insoluble salt of leuprolide, leuprolide oleate, was formed from aqueous leuprolide acetate and sodium oleate solutions. The insoluble salt was separated from the aqueous phase, dried and then added to the poly(d,l-lactide-co-glycolide) solution to form the first liquid preproduct, wherein the drug is dispersed and/or dissolved in the polymer solution. The first liquid preproduct is mixed with and dispersed in the second liquid preproduct. The use of the water-insoluble leuprolide salt resulted in high encapsulation efficiencies (>85%) and in an even more pronounced retardation in drug release in pH 7.4 phosphate buffer (simulates body fluids) when compared to the water-soluble salt, leuprolide acetate.

EXAMPLE 5

Preparation of Particles from Polymer-containing Emulsion and Biocompatible Liquid A w/o emulsion of a bupivcaine HCl-containing aqueous solution of chitosan (chitosan in an acidic medium or chitosan glutamate in water) in peanut oil with an emulsifying agent (Tween 80/Span 80) (syringe 1) is formed such that the chitosan is present in the droplets dispersed within the oil. The emulsion is then mixed with an alkaline aqueous phase (pH 7.4) (syringe 2) by connecting the two syringes with a connector or by screwing the two syringes together and by pushing the plungers forward and backward (25 mixing cycles). The extended release chitosan particles are thereby formed because of the pH-change in the aqueous droplets resulting in the precipitation of chitosan. The particle dispersion is then ready to be injected.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A ready-to-use single- or multi-dose dispersion composition comprising solidified particles that provide an extended release of one or more active compounds after administration to a subject; wherein
    a. the extended release solidified particles are formed by mixing at least two liquid preproducts, which are present in portions suitable for the preparation of the single- or multi-dose composition;
    b. the first liquid preproduct comprises a carrier material that solidifies to form the extended solidified release particles and, optionally, a biocompatible solvent or solvent mixture;
    c. the second liquid preproduct comprises a biocompatible liquid within which the first liquid preproduct forms the extended release solidified particles;
    d. one or more active compounds are independently included in the first liquid preproduct and/or the second liquid preproduct; and
    e. the extended release solidified particles are formed by mixing the preproducts prior to administration to the subject.

2. The composition of claim 1, wherein the extended release particles are further processed by concentrating the dispersion or changing the composition of the liquid in which the particles are dispersed prior to administration of the composition.

3. The composition of claim 1, wherein the dispersion is administered without further processing.

4. The composition of claim 1, wherein one or more additional solid or liquid preproducts is used for preparation of the composition and/or formation of the extended release particles.

5. The composition of claim 1, wherein the liquid preproducts are provided in separate chambers as primary packaging within a device.

6. The composition of claim 5, wherein the device is a multi-chamber syringe adapted for mixing of at least the first and second liquid preproducts and for administration of the ready-to-use composition.

7. The composition of claim 1, wherein the liquid preproducts are provided in separate chambers as primary packaging that are adapted for connection to each other to permit mixing of at least the first and second liquid preproducts.

8. The composition of claim 1, wherein the liquid preproducts are provided in separate containers.

9. The composition of claim 1, wherein the preproducts are provided in sterile form and mixing of the preproducts is conducted aseptically.

10. The composition of claim 1, wherein the carrier material is a polymer, a protein, a lipid, a wax, a non-polymeric material or a combination thereof.

11. The composition of claim 1, wherein an active compound in the dispersion is provided in dissolved, emulsified and/or suspended form in at least one of the first and second liquid preproducts.

12. The composition of claim 1, 2 or 4, wherein the composition is adapted for parenteral, peroral, rectal, buccal, ophthalmic, pulmonary, vaginal, nasal, local, sublingual, periodontal, topical, intralesional or transdermal administration, for the treatment of soft- and hard tissue defects, for the treatment of wounds, for use in tissue regeneration, for use as a tissue glue or for the filling of body cavities.

13. A method for the preparation of a ready-to-use single- or multi-dose-dispersion of extended release solidified particles that provide an extended release of one or more active compounds after administration to a subject, the method comprising the step of:
    a. providing at least two liquid preproducts;
    b. providing at least one active compound in dissolved, emulsified and/or suspended form in at least one of the at least two liquid preproducts;
    c. mixing at least two of the liquid preproducts, which are present in portions suitable for the preparation of the single- or multi-dose dispersion, to form a dispersion of a first liquid preproduct within a second liquid preproduct; wherein the first liquid preproduct comprises a carrier material that solidifies to form the extended release solidified particles and, optionally, a biocompatible solvent or solvent mixture; and the second liquid preproduct comprises a biocompatible liquid within which the first liquid preproduct forms the extended release solidified particles prior to administration to the subject.

14. The method of claim 13, further comprising the steps of:
    a. providing one or more additional solid or liquid preproducts prior to the step of mixing the first and second liquid preproducts.

15. The method of claim 13, further comprising the step of:
    a. forming the first liquid preproduct by dissolving the carrier material in a biocompatible solvent or solvent mixture prior to mixing the first liquid preproduct with the second liquid preproduct.

16. The method of claim 13, further comprising the step of:
    a. mixing the first and second liquid preproducts just prior to administration.

17. The method of claim 13, further comprising the step of:
    a. providing the first liquid preproduct as a dispersion comprising the carrier material, which is dissolved in a solvent or solvent mixture, dispersed in a liquid.

18. The method of claim 13, further comprising the step of:
    a. providing an active compound in dissolved, emulsified and/or suspended form in at least one of the first and second liquid preproducts prior to mixing the first liquid preproduct with the second liquid preproduct.

19. The method of claim 13, further comprising the step of:
a. providing at least the first and second liquid preproducts in separate chambers as primary packaging within a device.

20. The method of claim 13, further comprising the step of:
a. providing at least the first and second liquid preproducts in separate containers.

21. The method of claim 13, further comprising the step of:
a. concentrating the dispersion to obtain a higher number of particles per volume of dispersion.

22. The method of claim 13, further comprising the step of:
a. replacing a portion or substantially all of the liquid phase of the dispersion, after it is formed and before it is administered, with another biocompatible liquid.

23. The method of claim 13, further comprising the step of:
a. providing one or more substances selected from the group consisting of viscosity-increasing substances, substances that cause a thixotropic effect, stabilizers, emulsifying agents, release modifying agents, substances that change the residence time at the site of administration, bioadhesive materials, penetration enhancers, substances that reduce the solubility of the active compound, or substances that influence formation of the particles.

24. The method of claim 13, wherein the active compound is independently selected upon each occurrence from the group consisting of peptide-or protein drugs, oligonucleotides, gene therapeutical agents, antibiotics, anti-inflammatory agents, antiinfectives, antiparasitics, hormones, immunologically active compounds, vaccines, immunomodulators, immunosuppressants, anticancer agents, diuretics, drugs for the gastrointestinal tract, drugs for the heart or circulation, drugs for the respiratory tract, growth factors, interferons, analgesics, local anaesthetics and neuroactive drugs.

25. The method of claim 13, wherein the carrier material is a polymer, a protein, a lipid, a wax, a non-polymeric material or a combination thereof.

26. A method of administering a ready-to-use single- or multi-dose dispersion composition comprising solidified particles that provide an extended release of one or more active compounds, the method comprising the step of:
a. administering a composition according to any one of claim 1, 2, or 4.

27. The method of claim 26, wherein the composition is adapted for parenteral, peroral, rectal, buccal, ophthalmic, pulmonary, vaginal, nasal, local, sublingual, periodontal, topical, intralesional or transdermal administration, for the treatment of soft-and hard tissue defects, for the treatment of wounds, for use in tissue regeneration, for use as a tissue glue or for the filling of body cavities.

28. A method of administering a ready-to-use single- or multi-dose dispersion composition comprising solidified particles that provide an extended release of one or more active compounds, the method comprising the step of:
a. administering a composition prepared according to any one of claims 13, 14, 19 , or 20.

29. The method of claim 28, wherein the composition is adapted for parenteral, peroral, rectal, buccal, ophthalmic, pulmonary, vaginal, nasal, local, sublingual, periodontal, topical, intralesional or transdermal administration, for the treatment of soft-and hard tissue defects, for the treatment of wounds, for use in tissue regeneration, for use as a tissue glue or for the filling of body cavities.

30. A kit for the preparation of a ready-to-use single- or multi-dose dispersion of extended release solidified particles, the kit comprising at least two liquid preproducts each of which is present in a portion for the preparation of a single- or multi-dose composition; wherein
a. at least two of the preproducts are liquid and wherein the extended release solidified particles are formed by mixing the preproducts;
b. a first liquid preproduct comprises a carrier material that solidifies in a second liquid preproduct prior to administration to a subject to form the extended release solidified particles and, optionally, a biocompatible solvent or solvent mixture;
c. a second liquid preproduct comprises a biocompatible liquid within which the first liquid preproduct forms the extended release solidified particles prior to administration to a subject ; and
d. one or more active compounds are independently included in the first liquid preproduct and/or the second liquid preproduct.

31. The kit of claim 30 further comprising concentrating means adapted to concentrate the dispersion.

32. The kit of claim 30 further comprising liquid exchanging means adapted to exchange the liquid in the dispersion from a first liquid to a second liquid.

33. The kit of claim 30, wherein the liquid preproducts are provided in sterile form.

34. The kit of claim 30, wherein the carrier material is a polymer, a protein, a lipid, a wax, or a combination thereof.

35. The kit of claim 30, wherein an active compound in the dispersion is provided in dissolved, emulsified and/or suspended form in at least one of the first and second liquid preproducts.

36. The kit of claim 30 further comprising one or more additional solid or liquid preproducts for preparation of the composition and/or formation of the extended release particles.

37. The kit of claim 30, wherein the liquid preproducts are provided in separate chambers as primary packaging within a device.

38. The kit of claim 37, wherein the device is a multi-chamber syringe adapted for mixing of at least the first and second liquid preproducts and for administration of the ready-to-use composition.

39. The kit of claim 30, wherein the separate chambers are adapted for connection to each other to permit mixing of at least the first and second liquid preproducts.

40. The composition of claim 30, wherein the liquid preproducts are provided in separate containers.

41. The kit of claim 30, wherein the kit is adapted for parenteral, peroral, rectal, buccal, ophthalmic, pulmonary, vaginal, nasal, local, sublingual, periodontal, topical, intralesional or transdermal administration, for the treatment of soft- and hard tissue defects, for the treatment of wounds, for use in tissue regeneration, for use as a tissue glue or for the filling of body cavities.

42. The kit of claim 30, wherein the first liquid preproduct is provided as a dispersion of a carrier material, which is dissolved in a solvent or solvent mixture, within a liquid.

43. A kit of claim 34, wherein the carrier material is a cellulose, cellulose acetate, ethyl cellulose, cellulose acetate phthalate, hydroxypropylmethyl cellulose, acrylic acid, poly (methylmethacrylate), cyanoacrylate, polyanhydride, polyester, polylactide, polyglycolide, polycaprolactone, polyhydroxybutyrate, polyhydroxyvalerate, poly(lactide-co-glycolide-ethyleneglycol) block polymers, polyamine, polyaminoacid, polyorthoester, polyurethane, poly(ortho carbonate, polyphosphazene, polyacetal, polyketal, polyoxyethylene-oxypropylene, polysaccharide, sodium alginate, chitosan, chitin, polyethyleneglycol, polyvinylpyrrolidone, copolymer, terpolymer, derivatives thereof, or a combination of two or more of these carrier materials.

44. The kit of claim 34, wherein the carrier material comprises polylactide or a polylactide-derivative.

45. The kit of claim 30, wherein the first liquid preproduct comprises a biocompatible solvent or solvent mixture that dissolves the carrier material.

46. The kit of claim 30, wherein the second liquid preproduct comprises a natural, semisynthetic or synthetic lipid, oil or wax, cottonseed oil, soybean oil, safflower oil, hydrated peanut oil, olive oil, castor oil, triglyceride mixtures, medium chain triglyceride, monoglycerides, glycerolmonooleate, silicone oil, isopropylmyristate, ethyloleate, paraffins, water, glycerol, propylene glycol, polyethylene glycol or a combination of two or more of these substances as a major component.

47. The kit of claim 30, wherein the composition further comprises one or more substances selected from the group consisting of viscosity-increasing substances, substances that cause a thixotropic effect, stabilizers, emulsifying agents, release modifying agents, substances that change the residence time at the site of administration, bioadhesive materials, penetration enhancers, substances that reduce the solubility of the active compound, or substances that influence formation of the particles.

48. The kit of claim 30, wherein the active compound is independently selected upon each occurrence from the group consisting of peptide-or protein drugs, oligonucleotides, gene therapeutical agents, antibiotics, anti-inflammatory agents, antiinfectives, antiparasitics, hormones, immunologically active compounds, vaccines, immunomodulators, immunosuppressants, anticancer agents, diuretics, drugs for the gastrointestinal tract, drugs for the heart or circulation, drugs for the respiratory tract, growth factors, interferons, analgesics, local anaesthetics and neuroactive drugs.

* * * * *